(12) United States Patent
Murata

(10) Patent No.: US 7,556,604 B2
(45) Date of Patent: Jul. 7, 2009

(54) COGNITIVE CAPACITY MEASUREMENT DEVICE AND COGNITIVE CAPACITY MEASUREMENT METHOD

(75) Inventor: Tsutomu Murata, Koganei (JP)

(73) Assignee: National Institute of Information and Communications Technology, Tokyo (JP)

( * ) Notice: Subject to any disclaimer, the term of this patent is extended or adjusted under 35 U.S.C. 154(b) by 293 days.

(21) Appl. No.: 11/233,287

(22) Filed: Sep. 22, 2005

(65) Prior Publication Data
US 2006/0074340 A1    Apr. 6, 2006

(30) Foreign Application Priority Data
Sep. 24, 2004    (JP)    ............................ P2004-278225

(51) Int. Cl.
*A61B 13/00*    (2006.01)
(52) U.S. Cl. .................................................... 600/558
(58) Field of Classification Search ................ 600/300, 600/558, 544, 545, 26, 27; 351/222, 237–239
See application file for complete search history.

(56) References Cited

U.S. PATENT DOCUMENTS

| 7,211,050 B1 * | 5/2007 | Caplygin ..................... 600/558 |
| 2003/0073885 A1 | 4/2003 | Theodoracopulos et al. |

FOREIGN PATENT DOCUMENTS

| JP | 6-46989 | 6/1994 |
| JP | 2506023 | 4/1996 |

OTHER PUBLICATIONS

Szekely Anna, et al: "Timed Action and Object Naming" 2002, Technical Report CRL-0202, Center for Research in Language, University of California, San Diego, CA 92093-0526, XP002357384, p. 8, col. 2, lines 51-56; figure 4c. p. 11, col. 1, line 37—p. 11, col. 2, line 48*, p. 12, col. 2, lines 24-41.

Dell 'Acqua R, et al: "Naming Times and Standardized Norms for the Italian PD/DPSS set of 266 pictures: direct comparisons with American, English, French, and Spanish published databases." Nov. 2000, Behavior Research Methods, Instruments & Computers: A Journal of the Psychonomic Society, Inc., Nov. 2000, vol. 32, NR. 4, pp. 388-615, XP008056656; ISSN: 0743-3808, p. 590, col. 1, lines 7-35.

(Continued)

*Primary Examiner*—Max Hindenburg
*Assistant Examiner*—Brian Szmal

(57) ABSTRACT

A cognitive capacity measuring device utilizes an image display unit for displaying different kinds of images that have been degraded from an original photographic object. A subject can provide an input when he/she discerns the photographic object in the degraded image. Recognition time periods are recorded and matched with predetermined challenge level data parameters to calculate a cognitive capacity of the subject. A statistically significant number of test subjects provide recognition times relative to a specific degraded image so that a normal distribution from a frequency distribution of the number of subjects in relationship to a logarithm of the recognition times can be determined. The normal distribution along with the challenge level parameters can provide an indication of the subject's cognitive capabilities.

14 Claims, 14 Drawing Sheets

OTHER PUBLICATIONS

Laws, Keith R. et al: "The Effect of 'Masking' On Picture Naming." Cortex; A Journal Devoted to the Study of the Nervous System and Behavior, Apr. 2002, vol. 38, No. 2, Apr. 2002, pp. 137-147, XP008056538; ISSN: 0010-9452, the whole document.

Patterson, M.B. et al: "Performance of Elderly and Young Normals on the Gollin Incomplete Pictures Test." Perceptual and Motor Skills, Oct. 1999, vol. 89, No. 2, Oct. 1999, pp. 663-664, XP008056638, United States; ISSN: 0031-5125, the whole document.

Mack, J.L. et al: "Performance of Subjects with Probable Alzheimer Disease and Normal Elderly Controls on the Gollin Incomplete Pictures Test." Perceptual and Motor Skills, Dec. 1993, vol. 77, No. 3 Pt. 1, Dec. 1993, pp. 951-969, XP008056615. United States ISSN: 0031-5125, p. 954, line 37-p. 960, line 27.

* cited by examiner

| DEGRADED IMAGE | ORIGINAL IMAGE | PHOTOGRAPHIC OBJECT |
|---|---|---|
|  |  | SHIP |
|  |  | HORSE |
|  |  | CHICKEN |
|  |  | CAN |
|  |  | FAUCET |
|  |  | HUMAN FACE |

SUBJECT DATA MEMORY UNIT

| SUBJECT IDENTIFIER | AGE | SEX | NAME |
|---|---|---|---|
| 0001 | 25 | M | TARO YAMAMOTO |
| 0002 | 30 | F | HANAKO YAMADA |

FIG.5

IMAGE DATA MEMORY UNIT

| IMAGE IDENTIFIER | DEGRADED IMAGE | ORIGINAL IMAGE |
|---|---|---|
| 0001 | | |
| 0002 | | |

FIG.6

RECOGNITION TIME DATA MEMORY UNIT

| IMAGE IDENTIFIER | SUBJECT IDENTIFIER | RECOGNITION TIME |
|---|---|---|
| 0001 | 0001 | 1 |
| 0001 | 0002 | 2 |
| 0001 | 0003 | 2 |
| 0001 | 0100 | 1 |
| 0002 | 0001 | 2 |
| 0002 | 0002 | 2 |

FIG.7

CHALLENGE LEVEL DATA MEMORY UNIT

| IMAGE IDENTIFIER | MEAN VALUE | STANDARD DEVIATION |
|---|---|---|
| 0001 | -0.34 | 0.33 |
| 0002 | 0.01 | 0.44 |

FIG.8

COGNITIVE CAPACITY MEMORY UNIT

| SUBJECT IDENTIFIER | COGNITIVE CAPACITY SCORE |
|---|---|
| 0001 | 0.5 |
| 0001 | -0.4 |
| 0001 | 0.2 |

FIG.12 logt m=-0.34 m=0.01 m=0.39 m=0.82 m=1.24 m=2.34 s=0.62 s=-0.47

COGNITIVE CAPACITY MEASUREMENT DEVICE AND COGNITIVE CAPACITY MEASUREMENT METHOD

BACKGROUND OF THE INVENTION

1. Field of the Invention

The present invention relates to a cognitive capacity measurement device and cognitive capacity measurement method that measures the unique cognitive capacity of individuals in order to contribute to research on brain function.

2. Description of Related Art

In the past, various intelligence tests and aptitude tests such as those indicated in Japanese Examined Patent Application Publication No. Hei 06-046989 and U.S. Pat. No. 2,506,023 were proposed as methods to measure human aptitude and capacity, and were used for education, employment and welfare, etc.

SUMMARY OF THE INVENTION

In this regard, attention is not directed toward the micromechanisms of the brain, and therefore, although these methods can measure the differences between individuals, the results obtained for each individual cannot reflect the brain activity involved, and for that reason, the legitimacy of the methods cannot be explained from the perspective of brain function.

Meanwhile, when showing multiple subjects a variety of images to which specified processing had been conducted and measuring the time required in order to recognize the related content, the present inventor discovered the heretofore completely unknown fact that the order of subjects based on the recognition time did not depend on the type of image, and hardly fluctuated at all; and at the same time, the order of images based on recognition time did not depend on the subjects, and hardly fluctuated at all. Close scrutiny also revealed that the frequency distribution of the number of subjects in relation to the logarithm of the recognition time of the images could approximate a normal distribution, and that the standardized scores of the subjects were nearly fixed irrespective of the type of image. Then, the present inventor identified the fact that the unique cognitive capacity of each subject and the unique challenge level of the image could be quantified into the two variables of the cognitive capacity score and the challenge level parameter respectively, and demonstrated that a specific relation expression could be established between these and the recognition time.

Further, because a simple transformation of this relation expression has the same form as the relation expression for chemical reaction velocity, the present inventor believes that the cognitive capacity score and the challenge level parameters derived by the aforementioned method reflect brain function, suggesting the possibility that a new understanding of the mechanisms of the brain could be obtained by analogy with thermodynamics.

The present invention addresses the problems of using these facts to establish a method to measure the cognitive capacity to reconstruct from incomplete data original data explainable by correspondence to brain function, of applying these results to conduct research on brain function, and, in the future, of selecting and determining the suitability of training appropriate to each individual, and of contributing to early detection, etc. of diseases related to cognitive function such as Alzheimer type dementia.

Specifically, the cognitive capacity measurement device related to the present invention is characterized by comprising: an image display unit that has a function to display to a subject a degraded image that is an image in which degradation of the data for recognizing a significant photographic object has been caused by conducting a specified process on an original image having a significant photographic object; a receiving unit to receive from the subject the fact that the aforementioned photographic object has been recognized, and to output the reception signals; a recognition time calculator that receives the aforementioned reception signals from this receiving unit and calculates the recognition time, which is the time the subject requires to recognize the aforementioned photographic object; a challenge level data memory unit that memorizes the challenge level data, which is data related to the challenge level of the aforementioned degraded image in conjunction with recognition of the photographic object; and a cognitive capacity computer that conducts specified computations using the aforementioned recognition time calculated by the aforementioned recognition time calculator and the aforementioned challenge level data memorized in the aforementioned challenge level data memory unit, and that calculates the cognitive capacity score, which is an index that digitizes the cognitive capacity of each subject. Here, significant photographic object means a photographic object that the subject can express with words.

When this kind of device, the cognitive capacity scores of individuals can be measured using a simple configuration, and moreover, the results can be explained corresponding to brain function. Further, the results can play a role in brain function research, and in the future can be used in the selection and determination of the suitability of training appropriate to each individual, and can be used in early detection, etc. of diseases related to cognitive function such as Alzheimer type dementia.

It has been confirmed that the frequency distribution of the number of subjects in relation to the logarithm of the recognition time of the degraded image acquired from multiple subjects approximates a normal distribution curve, and it appears that the standardized scores of subjects on this normal distribution express the cognitive capacities of the subjects. Moreover, because it appears that the shorter the recognition the higher the cognitive capacity, it is easier to understand and thus preferable to invert the sign of the numerical value of the standardized score and to use this number as the cognitive capacity score.

A preferable method to calculate recognition time can eliminate such factors as the physical reflex velocity of the subject by subtracting the time required for the original image from the time required for the degraded image.

Because the cognitive capacity score is unique to the individual, to effectively use this cognitive capacity score in training, etc., it is preferable to further provide a cognitive capacity memory unit that relates and memorizes the aforementioned cognitive capacity score and a subject identifier.

To improve the reliability of the measured results, it is desirable that the aforementioned image display unit selectively displays multiple types of images, and that the aforementioned cognitive capacity calculator calculate the cognitive capacity score from various recognition times obtained for each of the aforementioned degraded images.

As a specific embodiment, it is preferable to further provide an output device to output the aforementioned cognitive capacity scores.

It is preferable to segment the aforementioned original image to make aforementioned degraded image. This kind of image can be easily produced in large quantities, and the challenge level can be adjusted by adjusting the threshold value.

Moreover, in order to calculate the aforementioned challenge level data of the degraded images used in cognitive capacity measurements, a cognitive capacity measurement device of degraded images may be used that provides: an image display unit that has a function to display to a subject these degraded images; a receiving unit to receive from the subject the fact that the aforementioned photographic object has been recognized, and to output the reception signals; a recognition time calculator that receives the aforementioned reception signals from this receiving unit and calculates the recognition time, which is the time the subject requires to recognize the aforementioned photographic object; a recognition time data memory unit to memorize the respective recognition time data, which are data relating the aforementioned recognition times of multiple subjects that are calculated by this recognition time calculator; and a challenge level data computer that calculates challenge level data, which is data related to the challenge level of the aforementioned degraded image in conjunction with recognition of the photographic object, by obtaining the aforementioned recognition time data memorized in this recognition time data memory unit and approximating the aforementioned recognition time distribution form using a specified function.

Because experiments have confirmed that the frequency distribution of the number of subjects in relation to the logarithm of the recognition time of the degraded image acquired from multiple subjects closely approximates a normal distribution, it is possible to take the data that specifies this normal distribution as the challenge level data of the degraded image. Moreover, experiments have revealed that the standard deviation of this normal distribution can be approximated by a linear function of the mean value, and therefore this mean value can be used as the challenge level parameter. This way, the challenge level of the degraded image can be expressed by one variable, and the challenge levels of various degraded images are easy to compare.

Because the challenge level data is of unique degraded images, to effectively use this challenge level data in cognitive capacity measurements, it is preferable to further provide a challenge level data memory unit to relate and memorize the aforementioned challenge level data with a degraded image identifier.

According to the present invention, it is possible to measure the cognitive capacity to reconstruct original data from incomplete data. Moreover, the cognitive capacity score obtained by this method can explain the correlation to brain function, and therefore it is possible for these results to play a role in research on brain function. Further, in the future it will be possible to select and determine the suitability of training appropriate for each individual, and to contribute to the early discovery of diseases related to cognitive function such as Alzheimer type dementia.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 5 is a data structure diagram indicating the internal data of a subject data memory unit of the same embodiment;

FIG. 6 is a data construction diagram indicating the internal data of an image data memory unit of the same embodiment;

FIG. 7 is a data construction diagram indicating the internal data of a recognition time data memory unit of the same embodiment;

FIG. 8 is a data construction diagram indicating the internal data of a challenge level data memory unit of the same embodiment;

FIG. 12 is a data structure diagram indicating the internal data of a cognitive capacity memory unit of the same embodiment;

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Embodiment 1

Figure 1:
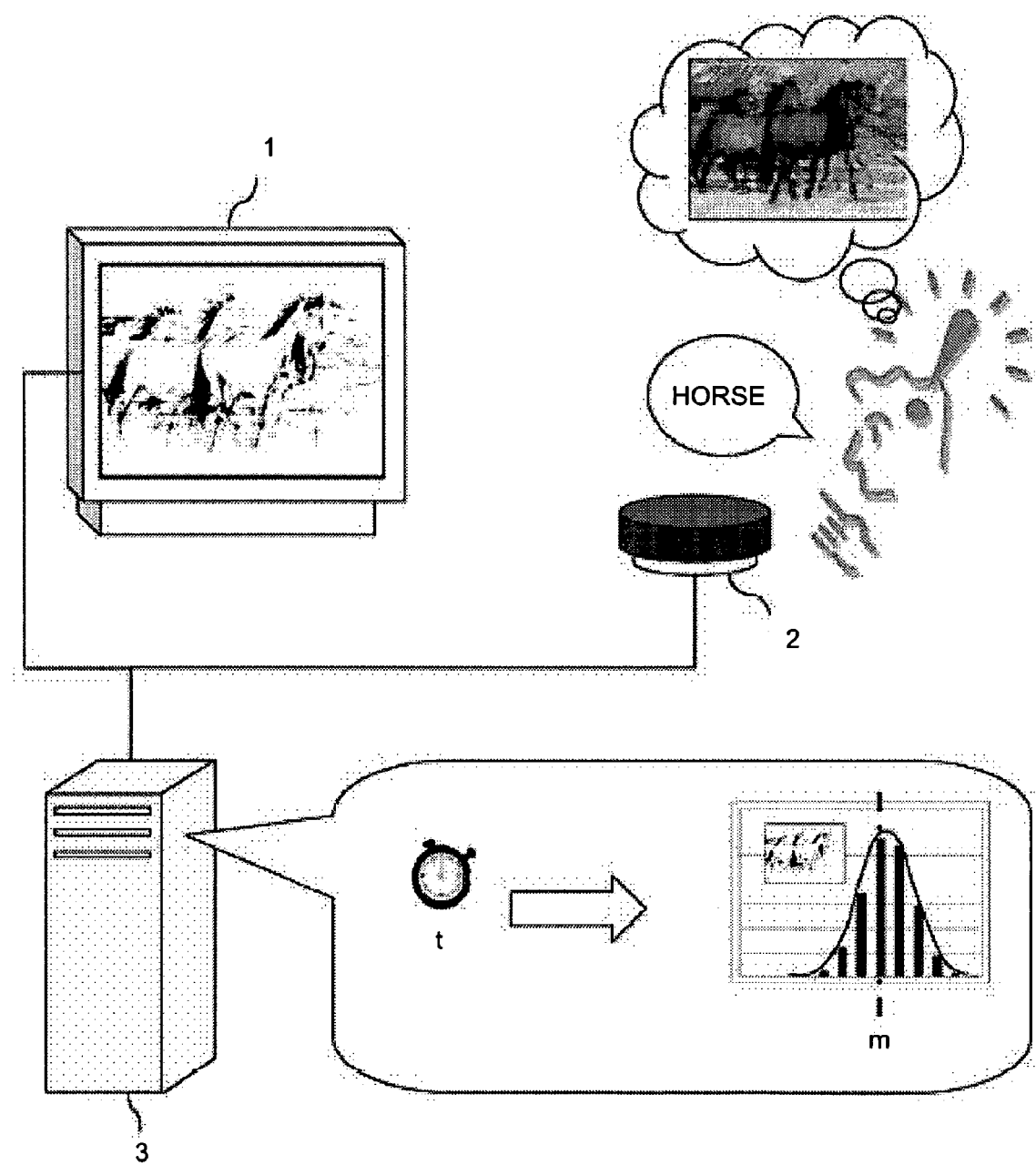
FIG. 1 is a schematic configuration diagram of a challenge level measurement device of a first embodiment of the present invention.

The present embodiment was made in order to calculate the unique challenge level parameter of an image from a frequency distribution of test results of multiple subjects in relation to a logarithm of the recognition times of the photographic object of the degraded image. FIG. 1 is a schematic configuration diagram indicating the challenge level measurement device of the present embodiment. This challenge level measurement device comprises: an image display unit 1 that displays to a subject for a specified time an original image having a significant photographic object and a degraded image that is an image in which specified processing has been conducted on the aforementioned original image to alter the original image so that only a part of the original image remains in the data for providing the aforementioned photographic object has been degraded; a receiving unit 2 to receive from the subject an input that the aforementioned photographic object has been recognized; and a data processing device 3 that receives the reception signals from this receiving unit 2 and conducts specified data processing based thereon.

The image display unit 1 is configured using a display 104, and is communicably connected to the aforementioned data processing device 3 in this embodiment, and displays one of the aforementioned original images or aforementioned degraded images based on commands from the data processing device 3. The aforementioned original images and aforementioned degraded images are, for example, like those indicated in FIG. 2.

The receiving unit 2 uses, for example, a push button type switch like that indicated in FIG. 1, and when the subject pushes the aforementioned switch, a reception signal is output. Further, the subject responds with the photographic object prior to pressing the aforementioned switch, and if this response is incorrect, the operator conducts processing that makes that response invalid.

Figure 3:
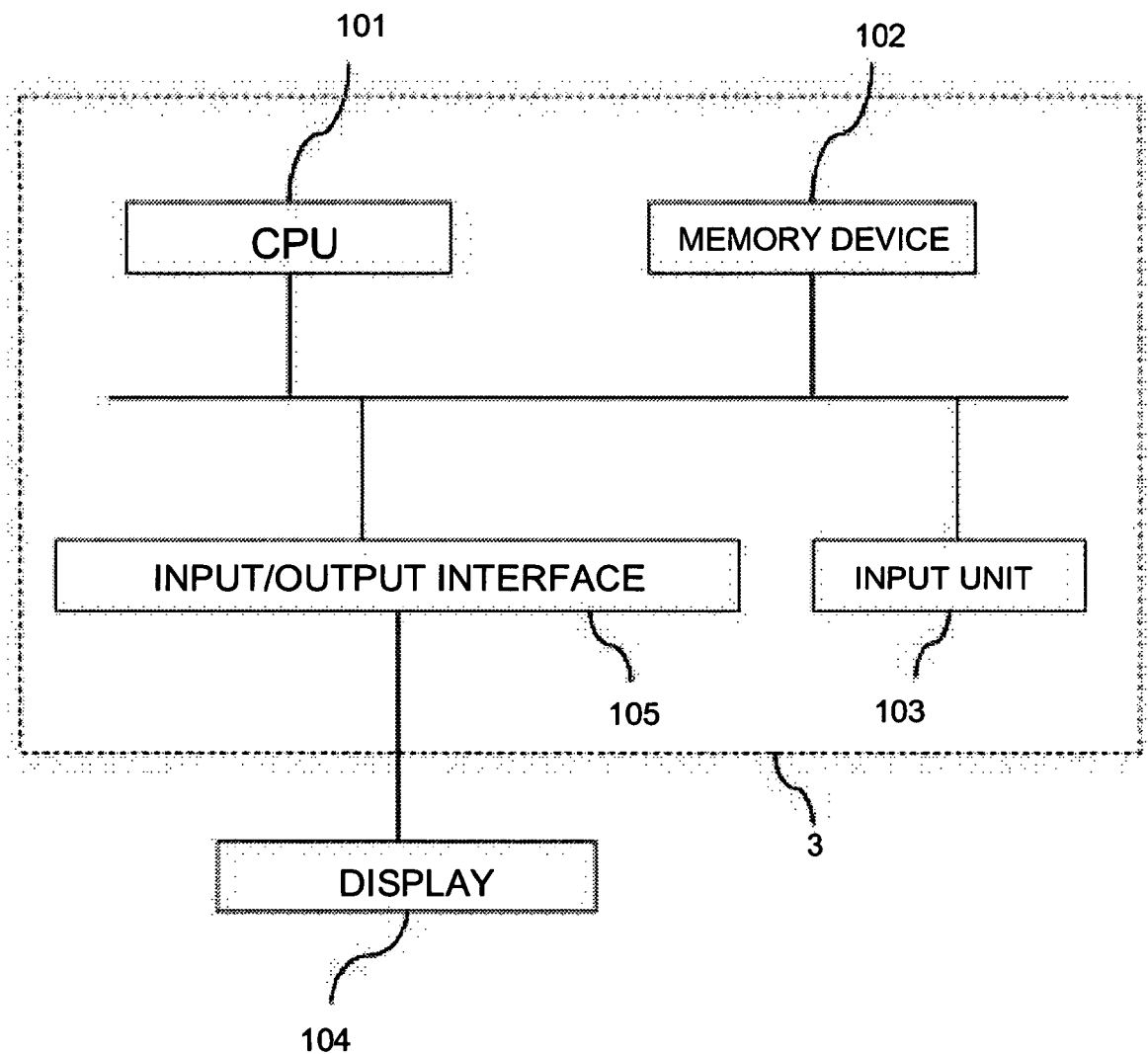
FIG. 3 is a schematic configuration diagram indicating the internal configuration of a data processing device of the same embodiment.
Figure 4:
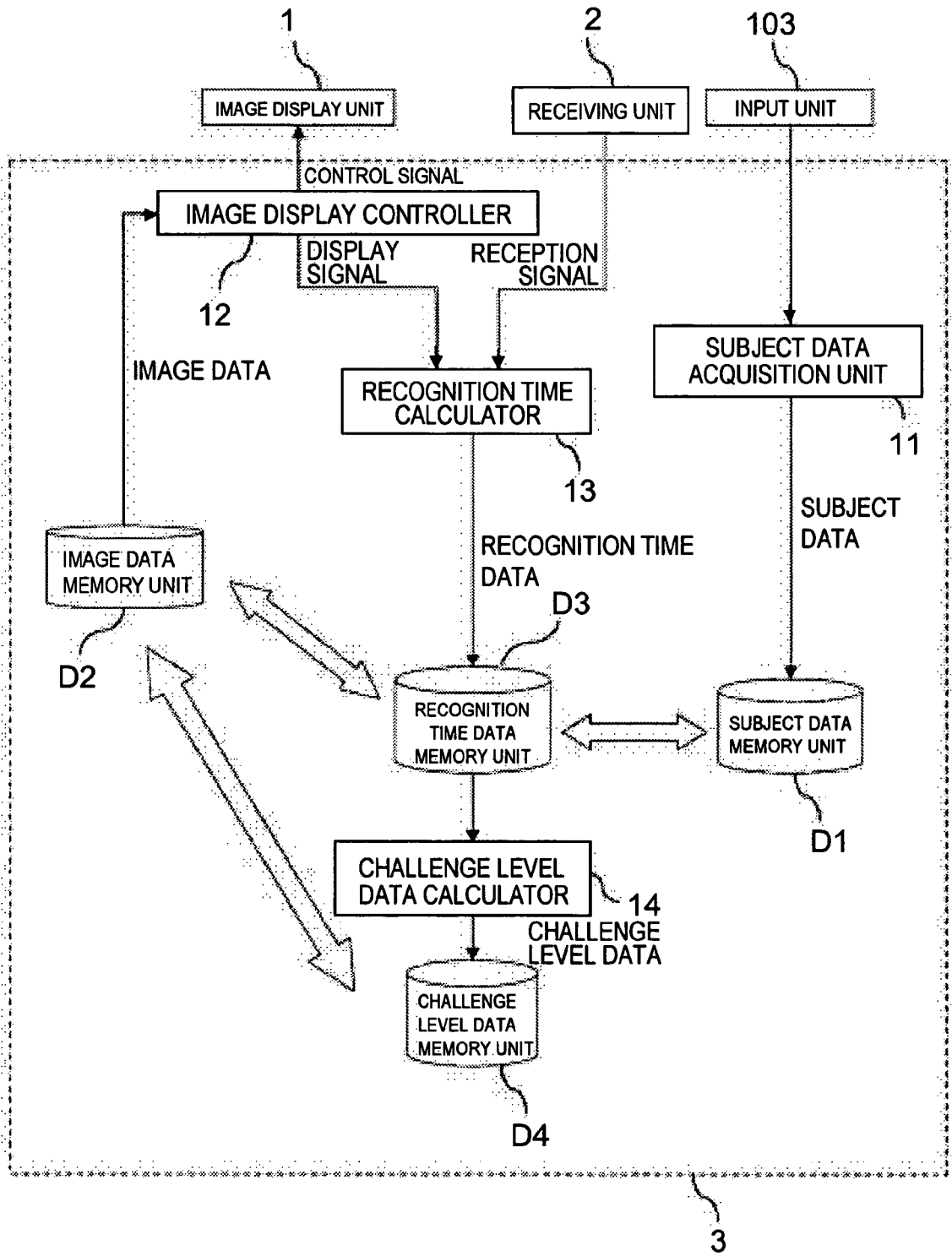
FIG. 4 is a functional block diagram of a data processing device of the same embodiment.

As indicated in FIG. 3, in addition to the CPU 101, the data processing device 3 comprises a volatile memory and a memory device such as an HDD 102, and further has an input units 103 that are a mouse and keyboard, etc., and an input/output interface 105, etc. for connecting to the aforementioned display 104. Then, a specified program is installed in the aforementioned memory device, the CPU 101 and the peripheral devices are coordinated based on this program, and as indicated in the functional block diagram in FIG. 4, this data processing device 3 is comprised to manifest the functions of a subject data acquisition unit 11, a subject data memory unit D1, an image data memory unit D2, an image display control unit 12, a recognition time calculator 13, a recognition time data memory unit D3, a challenge level data calculator 14, a challenge level data memory unit D4, etc.

Further, the aforementioned image display unit 1, receiving unit 2, and data processing device 3 do not have to be provided in a physically separated manner, and may be configured and used in a single unit such as, for example, a lap top computer.

Each unit will be described concretely in detail.

The subject data acquisition unit 11 receives the subject data such as the age, sex and name of the subject, provides the received subject data with an identifier (number, etc.) for identifying the subject (refer to FIG. 5), and stores these in the subject data memory unit D1 provided in a specified region of the aforementioned memory device.

Figure 2:
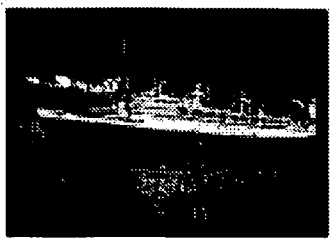
FIG. 2 is an explanatory diagram of an image displayed in the same embodiment.
Figure 2:
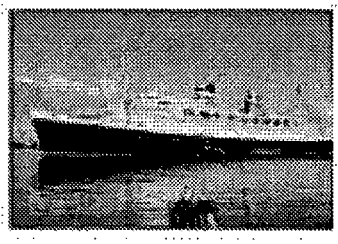
Figure 2:
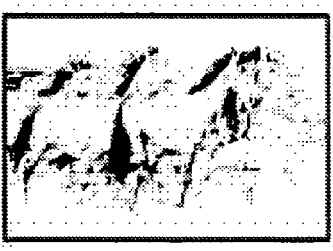
Figure 2:
Figure 2:
Figure 2:
Figure 2:
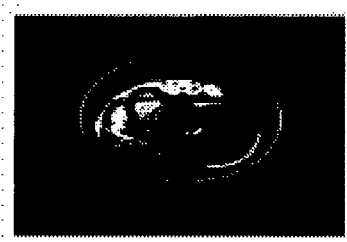
Figure 2:
Figure 2:
Figure 2:
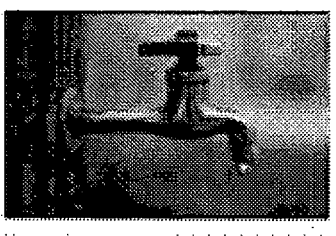
Figure 2:
Figure 2:

The image data memory unit D2 is provided in a specified region of the aforementioned memory device, and as indicated in FIG. 2, relates and stores the image data for displaying the various images to an image identifier for identifying the various images (refer to FIG. 6).

The image display control unit 12 displays the various images by using control signals to control the image display unit 1 based on the image data memorized in the aforementioned image data memory unit D2, and also outputs display signals to the recognition time calculator 13.

The recognition time calculator 13 calculates the time the subject requires to look at the degraded image and to recognize the photographic object. In the present embodiment, the recognition time calculator is configured to receive display signals from the aforementioned image display unit 12 and reception signals from the reception unit 2, to measure the times required from displaying the image to the subject pressing the switch for the degraded image and for the original image thereof, and to calculate the recognition time by subtracting the time required for the original image from the time required for the degraded image. This eliminates such factors as the physical response velocity of the subject. The calculated recognition times are related to the image identifier and the subject identifier, and stored in a specified format in the recognition time data memory unit D3 (refer to FIG. 7).

The challenge level data calculator 14 receives recognition time data from the recognition time data memory unit D4, finds a normal distribution in the frequency distribution of the number of subjects in relation to the logarithm of the recognition time for every image, and for example, outputs the mean value m and the standard deviation σ of this normal distribution as the challenge level data.

Here, the normal distribution is represented by the formula 1 below.

$$f(x) = \frac{1}{\sqrt{2\pi}\,\sigma} \exp\left(-\frac{(x-m)^2}{2\sigma^2}\right) \quad \text{[Formula 1]}$$

Further, because experiments by the present inventor revealed that the standard deviation σ can be approximated by the linear function of the mean value m, only the mean value m may be output as the challenge level data. The present inventor named this mean value m the challenge level parameter. This challenge level parameter is equivalent to the recognition time in logarithmic time in which half of the subjects recognize the photographic object, and is an index that expresses the cognitive difficulty of the degraded images.

The challenge level data memory unit D4 relates and memorizes the challenge level data calculated by the challenge level data calculator 14 to the image identifier (refer to FIG. 8).

Figure 9:
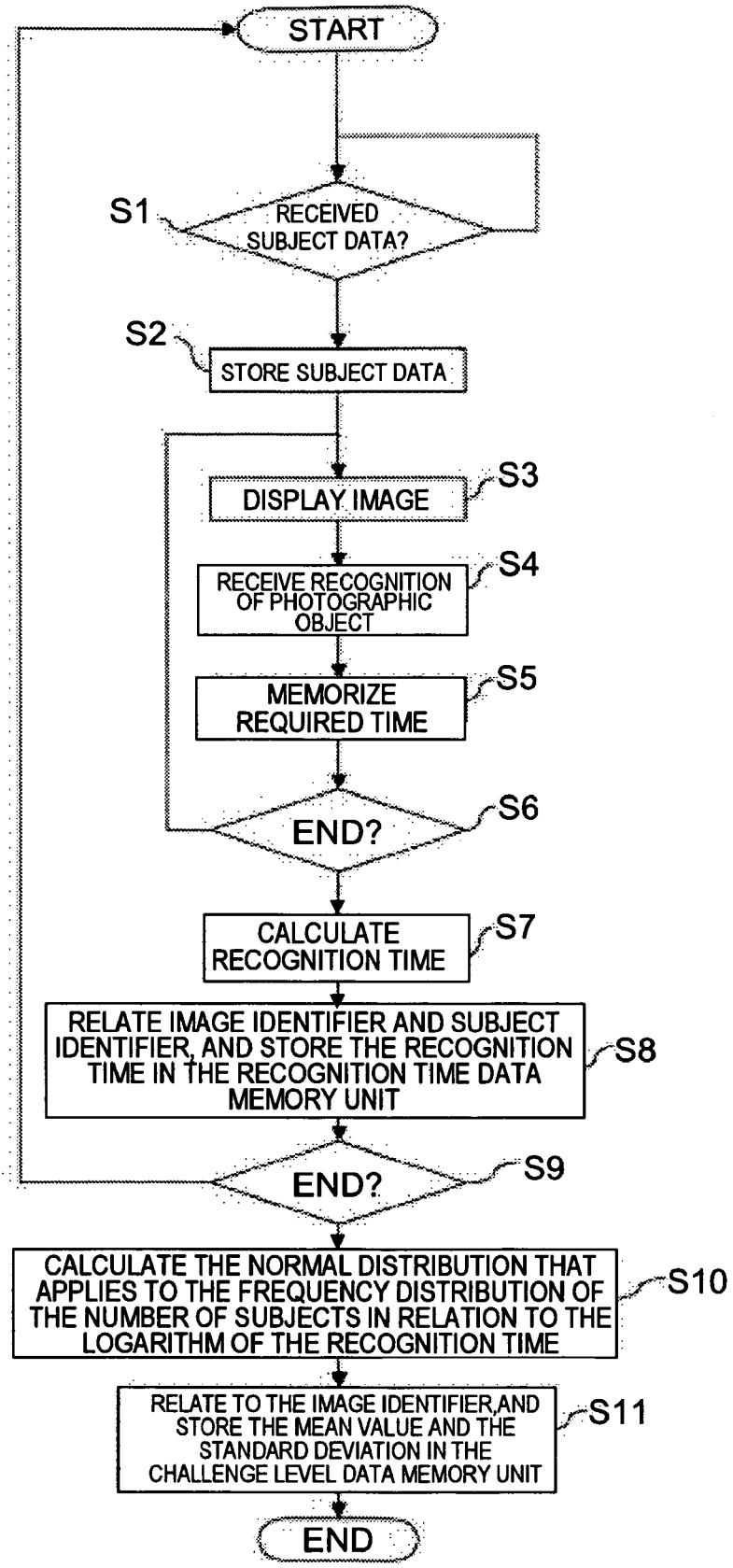
FIG. 9 is a flowchart indicating the operational steps of a challenge level measurement device of the same embodiment.

Next, the action of this device will be briefly explained by referring to FIG. 9.

First, the operator manipulates the input unit to enter the subject data.

The subject data acquisition unit 11 receives the subject data input in this way (step S1), and stores this in the subject data memory unit D1 (step S2).

Next, one of the degraded images or original images is displayed by the mage display unit 1 based on the command of the image display controller 12 (step S3).

Meanwhile, the subject looks at the displayed image, responds regarding that photographic object, and the fact that the photographic object has been recognized is entered by manipulating the receiving unit 2 (step S4).

The recognition time calculator 13 receives the display signals from the image display controller 12 and the reception signals from the receiving unit 2, acquires the required time, relates the required time data to the image identifier and the subject identifier, and memorizes this in the required time data memory unit not indicated in the diagram (step S5). When the required time data has been memorized or the specified time limit has lapsed, then steps S3 to S6 are repeated for all of the images.

After completing the tests for all of the images, the recognition time calculator 13 receives the required time data from the aforementioned required time memory unit, calculates the recognition time by subtracting the corresponding original image required time from the degraded image required time (step S7), and memorizes this as the recognition time data in the recognition time data memory unit D3 (step S8).

The test above is repeated for all of the subjects. (Step S9)

After completing the tests for all of the subjects, the challenge level data calculator 14 acquires the recognition time data from the recognition time data memory D3, fits the frequency distribution of the number of subjects to the logarithm of the recognition time for every image into a normal distribution, calculates, for example, the mean value m and standard deviation σ of this normal distribution as the challenge level data (step S10), and relates the data to an image identifier and stores this in the challenge level data memory unit D4 (step S11).

Embodiment 2

Figure 10:
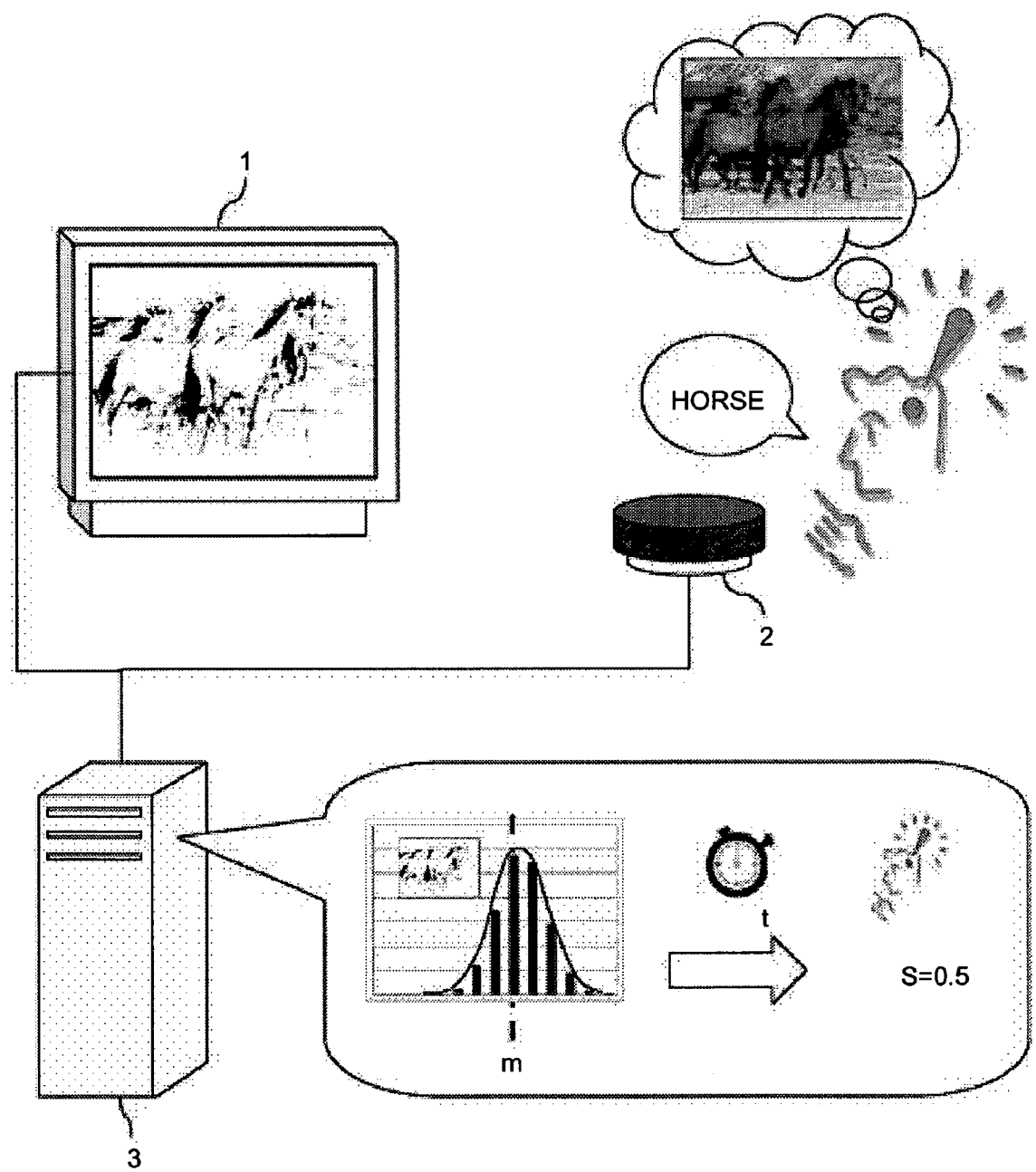
FIG. 10 is a schematic configuration diagram of a challenge level measurement device of a second embodiment of the present invention.

The present embodiment is configured so that the cognitive capacity of the subject is measured using challenge level data calculated by Embodiment 1. FIG. 10 is a schematic configuration diagram indicating the cognitive capacity measurement device of the present embodiment. In the same way as in Embodiment 1, this cognitive capacity measurement device comprises: an image display unit 1 that displays to a subject for a specified time an original image having a significant photographic object and a degraded image that is an image in which specified processing has been conducted on the aforementioned original image and the data for recognizing the aforementioned photographic object has been degraded; a receiving unit 2 to receive from the subject the fact that the aforementioned photographic object has been recognized; and a data processing device 3 that receives the reception signals from this receiving unit 2 and conducts specified data processing based thereon.

Here, the subject in the present embodiment is not limited to subjects for whom the recognition time is measured in order to calculate the challenge level in Embodiment 1, and may be other people. Specifically, this cognitive capacity measurement device is effective for subjects who do not contribute to the calculation of challenge level data, and if the recognition times are measured and the challenge level data of images are calculated for sufficiently many subjects according to Embodiment 1, the cognitive capacities of new subjects can be calculated using these images.

Figure 11:
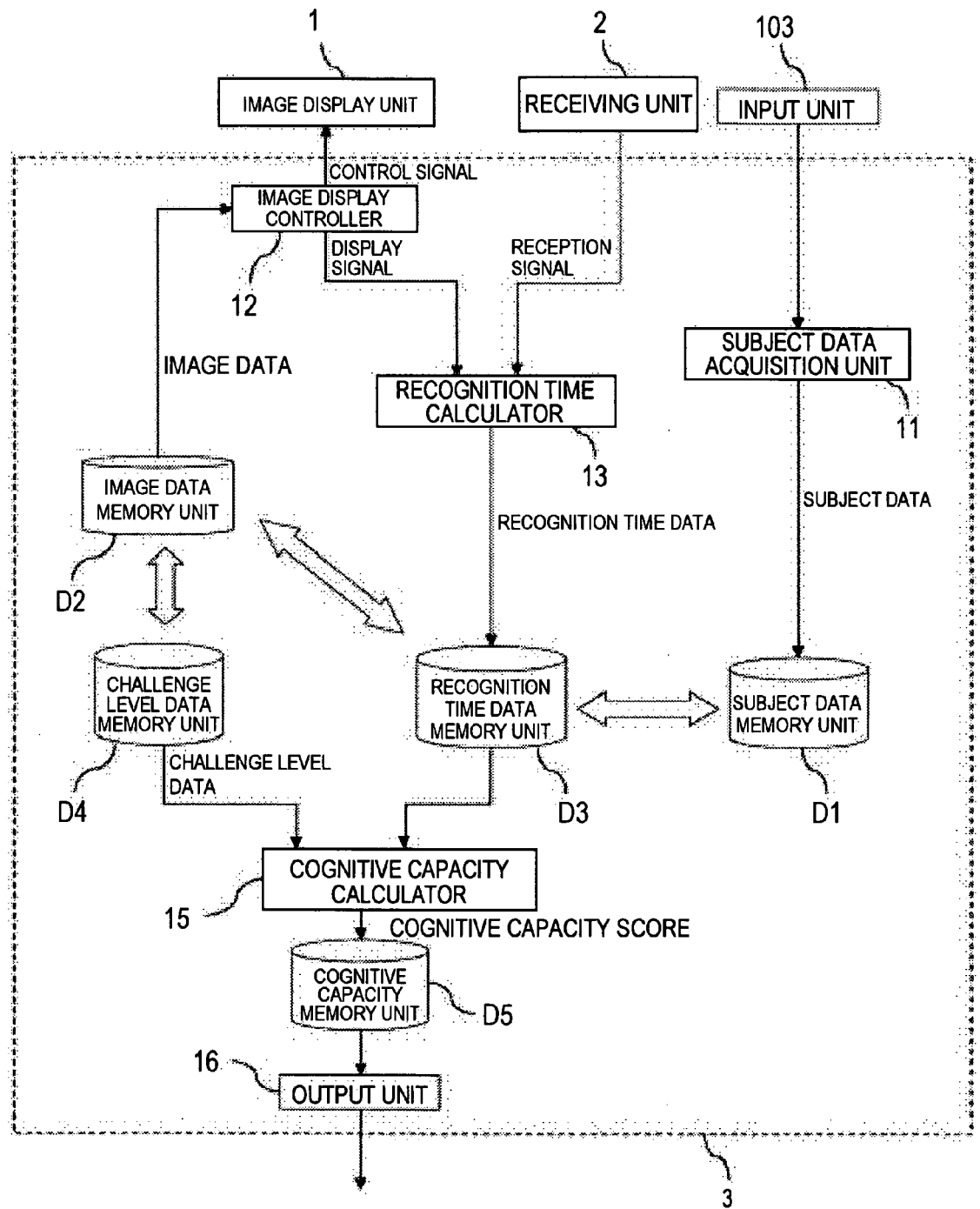
FIG. 11 is a functional block diagram of a data processing device of the same embodiment.

The various parts of the present embodiment will be described in detail while referring to FIG. 11, which is a functional block diagram of the data processing unit 3 in the present embodiment, and because there are many parts of the present embodiment that are the same as in Embodiment 1, the description will be confined to the points of difference from Embodiment 1, namely, the challenge level data memory unit D4, the cognitive capacity calculator 15, the cognitive capacity memory unit D5, and the output unit 16.

The challenge level data memory unit D4 relates and memorizes the challenge level data calculated in Embodiment 1 with an image identifier.

The cognitive capacity calculator 15 uses the recognition time data of the subject memorized in the recognition time data memory unit D3 and the challenge level data memorized in the challenge level data memory unit D4 to calculate the capacity score s of the subject based on the following Formula 2. Here, t is the recognition time, and m and σ are the challenge level data of the corresponding image, specifically, the mean value and standard deviation of the aforementioned normal distribution. The sign of the value called the standardized score is generally inverted to make this capacity score. The standardized score indicates the position at which the subject in question stands within the group of subjects that contributed to the challenge level data calculation in Embodiment 1. The present inventor discovered by experiment that the standardized score of a given subject is a nearly fixed value independent of the image. This indicates that this standardized score is an index of the cognitive capacities of the subjects. The capacity score is made by inverting the sign of the standardized score because it appears that the shorter the recognition time, the higher the cognitive capacity. For example, a subject positioned exactly at the mean would have a capacity score of 0. Further, in order to improve reliability, measurements based on multiple images are necessary, and therefore, in this case the mean value of the capacity scores calculated for every image shall be taken as the capacity score of the subject in question.

$$s = -\frac{\log t - m}{\sigma}$$

The cognitive capacity memory unit D5 relates and memorizes the cognitive capacity score calculated by the cognitive capacity calculator 15 with the subject identifier (refer to FIG. 12).

The output unit 16 uses a display or printer, etc. to output the cognitive capacity scores memorized in the cognitive capacity memory unit D5.

Figure 13:
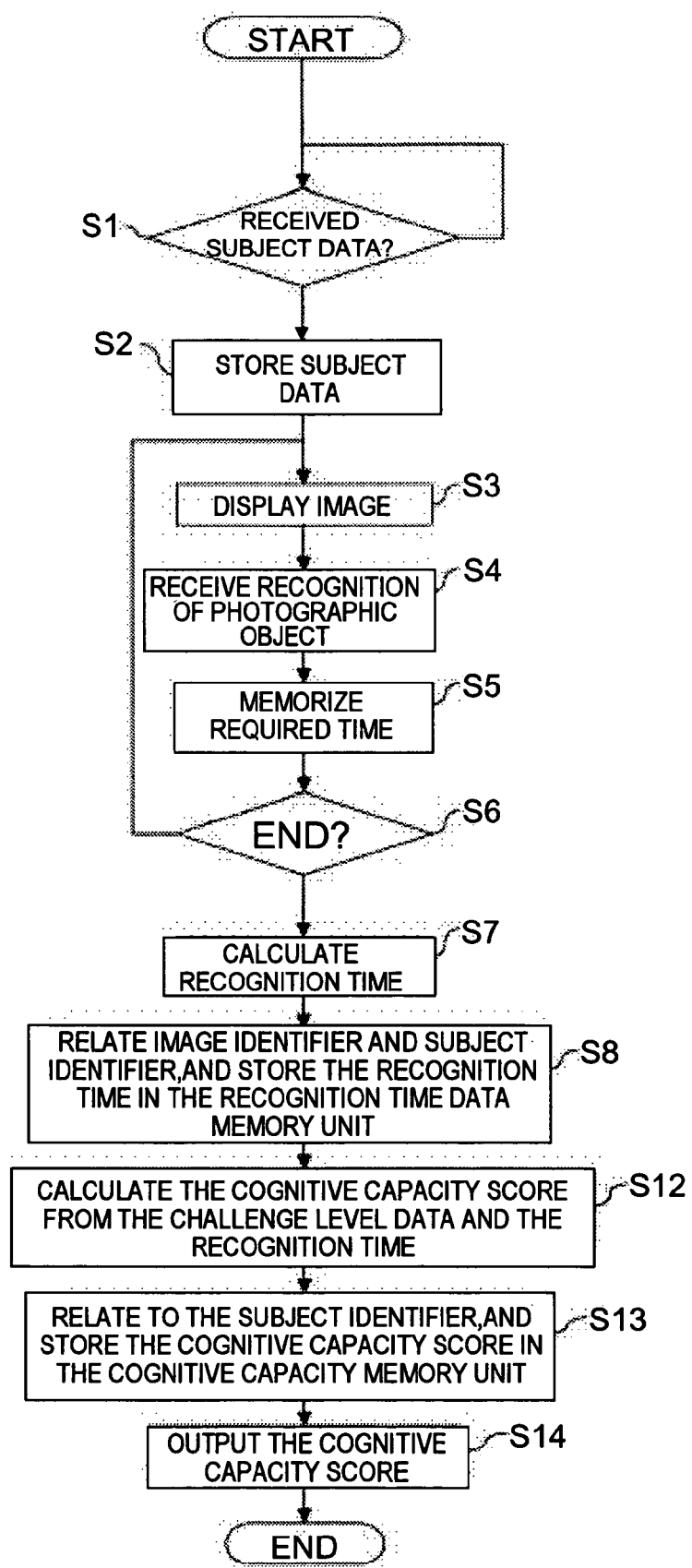
FIG. 13 is a flowchart indicating the operational steps of a challenge level measurement device of the same embodiment.

Next, the action of this device will be briefly explained by referring to FIG. 13.

Steps S1 to S8 are the same as in Embodiment 1. Moreover, when calculating the cognitive capacity of a subject for whom the recognition time has already been measured in Embodiment 1, this operation may be omitted because the recognition time data memorized in the recognition time data memory unit D3 may be used.

The cognitive capacity calculator 15 calculates the cognitive capacity score of the subject from the recognition time data memorized in the recognition time data memory unit D3 and the challenge level data memorized in the challenge level data memory unit D4 (step S12), and stores this in the cognitive capacity memory unit D5 (step S13).

The output unit 16 outputs the cognitive capacity score (step S14).

In this way, the challenge level parameters of the images are calculated by Embodiment 1, and the cognitive capacity scores of the subjects are calculated by Embodiment 2. By analogy with thermodynamics, the present inventor has indicated as follows the fact the challenge level parameter and the cognitive capacity score derived in this way reflect brain function. Specifically, the following relational equation Formula 3 may be established between the challenge level parameter, the cognitive capacity score and the recognition time. Here, A and B are constants derived by experiment.

$$t = A\exp(m(1-Bs)) \quad \text{Formula 3}$$

The recognition velocity v shall be the reciprocal of this recognition time t, and if S=1−Bs, the following Formula 4 is established.

$$v = \frac{1}{t} = \frac{1}{A}\exp(-mS) \quad \text{[Formula 4]}$$

This equation has the same form as the chemical reaction velocity equation represented in Formula 5 below. Here, v0 is the initial velocity, ΔE is the activated energy, $k_B$ is Boltzmann's constant, and T is the temperature.

$$v = v_0 \exp\left(-\frac{\Delta E}{k_B T}\right) \quad \text{[Formula 5]}$$

From the correspondence of these relational equations, the present inventor thinks that the cognitive capacity score of the subject corresponds to the temperature, that is, to the way that the number of micro-states increase, and the challenge level parameter of the images corresponds to the active energy. Further, the present inventor believes that the capacity score probably plays a role like the temperature of the search activity of the data space (memory space), and this suggests the possibility that new discoveries regarding brain function could be obtained by considering an analogy with thermodynamics.

In this way, according to the present invention, it is possible to digitize the cognitive capacity of the individual and the challenge level of the image by the heretofore unknown simple method of measuring recognition time of degraded images. Moreover, because the relational equation that determines the recognition time has been demonstrated, it will be possible to obtain new discoveries regarding brain function based on further research using the present invention. The present invention may also contribute to research on brain function, and in the future may be expected to play a role in the selection and determination of the suitability of training appropriate to individuals, and in the early discovery of illnesses related to cognitive function such as Alzheimer type dementia, etc.

Next, experiments will be explained in which the challenge level parameters and capacity scores were actual calculated according the present invention.

<Experiment 1> Calculation of the Challenge Level Parameter

Figure 14:
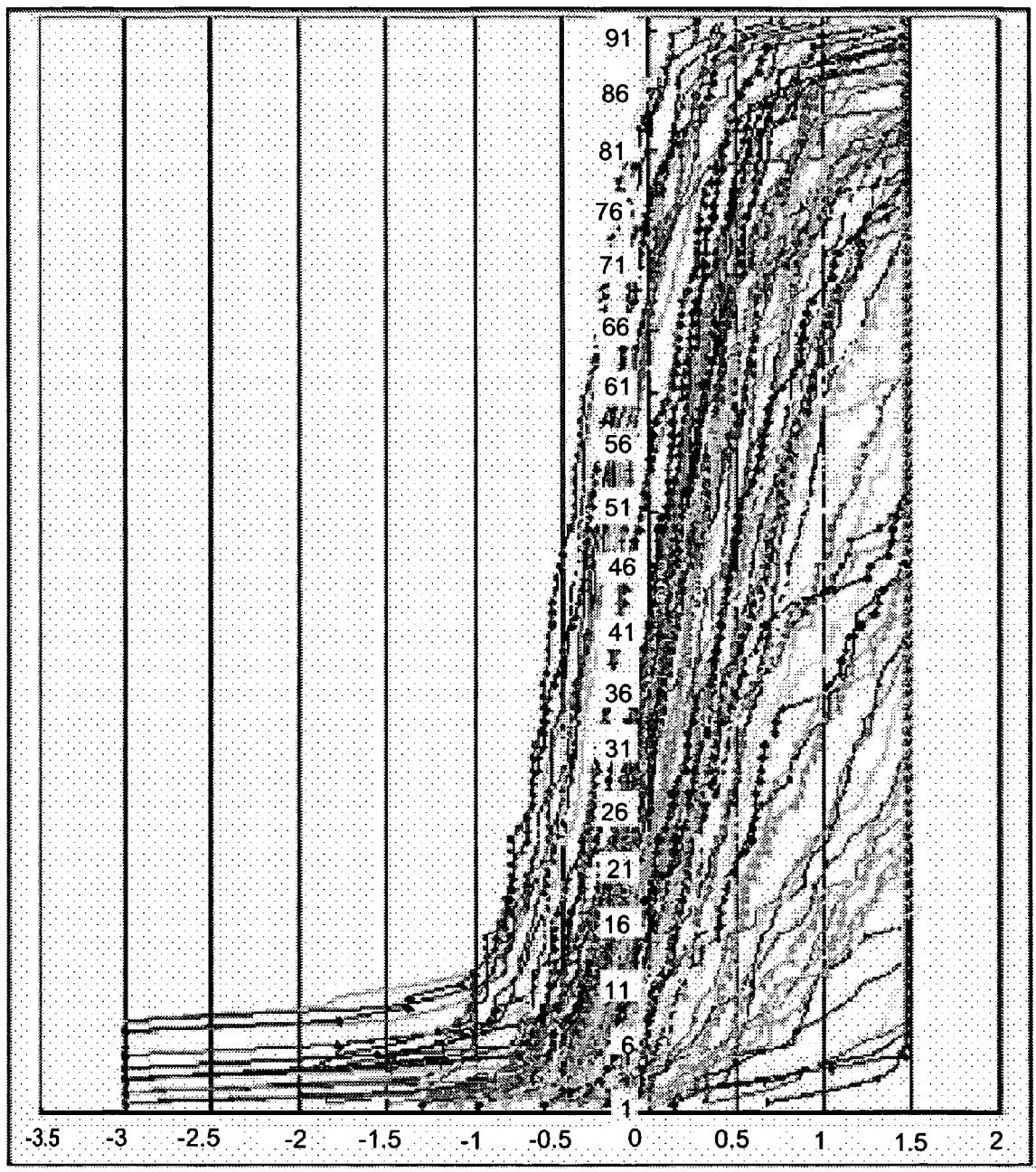
FIG. 14 is a cumulative histogram indicating the results of experiment 1 conducted using the challenge level measurement device of the first embodiment of the present invention.

The recognition times of 91 subjects (20 to 24 years) were measured using 90 groups of images, and the challenge level parameters of the images were calculated. FIG. 14 indicates the cumulative frequency distribution of the subjects in relation to the logarithm of the recognition times.

Figure 15:
FIG. 15 is part of the challenge level parameters that were calculated from the results of experiment 1 conducted using the challenge level measurement device of the first embodiment of the present invention.
Figure 15:
Figure 15:
Figure 15:
Figure 15:
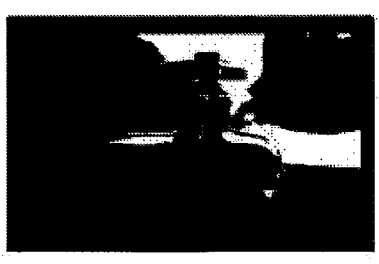
Figure 15:
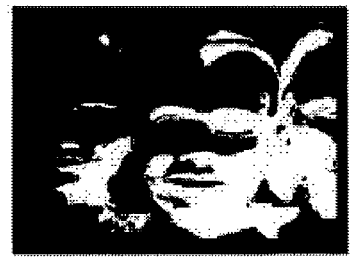

FIG. 15 indicates one part of the challenge level parameters of the images calculated in the experiment.

In addition, from the results of the experiment the approximation equation of Formula 6 below was obtained as an approximation equation that is established between the standard deviation a and the challenge level parameter m.

$$\sigma = 0.315m + 0.443 \quad \text{Formula 6}$$

<Experiment 2> Study of Calculated Capacity Scores

The measured values of the recognition times for images with pre-known challenge levels that were not used when calculating the capacity scores were compared with the estimated values obtained from Formula 3 in regard to subjects with calculated capacity scores. Here, the estimated value of the recognition times obtained from Formula 3 were A=0.0305 seconds and B=0.031 seconds.

Figure 16:
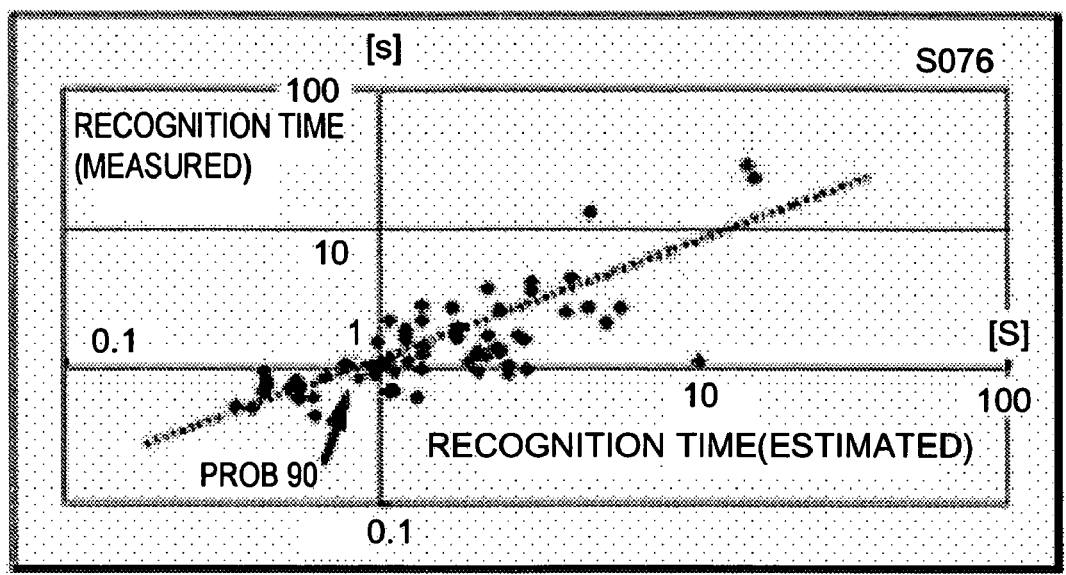
FIG. 16 is a diagram representing the results of experiment 2 conducted to confirm the reliability of the present invention.
Figure 16:
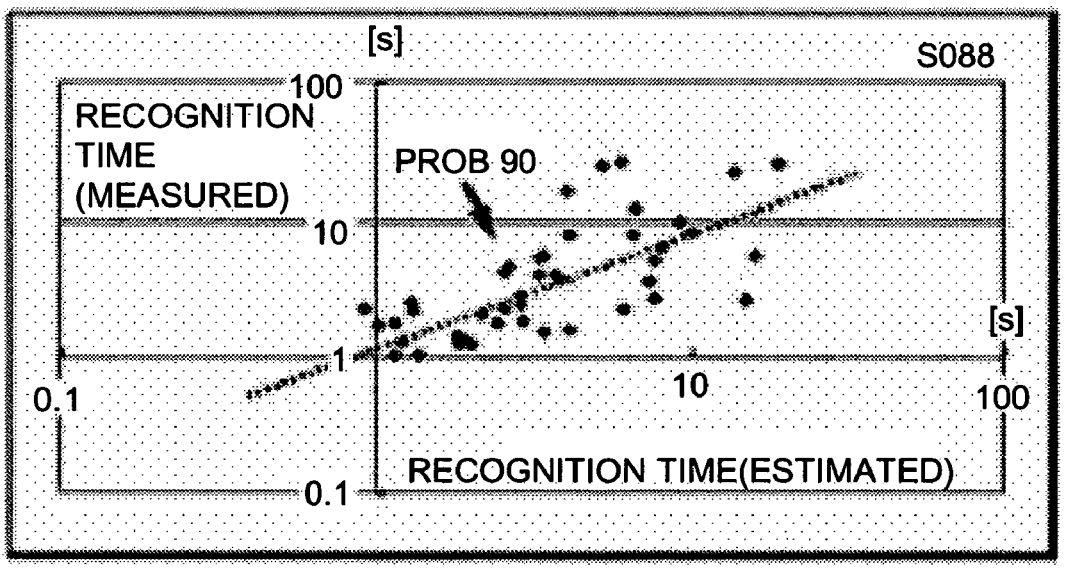

FIG. 16 indicates the relationship between the estimated values and the measured values of the recognition times for two subjects with differing capacity scores. The straight line indicating the estimated values represented in the diagram and the distribution of the point groups indicating the measured values demonstrate that the recognition times are effectively estimated.

Further, the present invention is not limited to the embodiments above. For example, the accuracy in the calculation of the challenge level parameters and the capacity scores could be improved by suitably eliminating data that differs from the trends at the extremes.

In addition, the median value may be used as the challenge level parameter to calculate the challenge level parameters. The median value is generally not affected by extreme values, and is satisfactory.

The present invention may have a variety of other forms within the range that does not deviate from the purpose thereof.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A cognitive capacity measurement device comprising:
   an image display unit that has a function to display to a subject a degraded image that is an image in which degradation of the data for recognizing a significant photographic object has been caused by conducting a specified process on an original image having the object;
   a receiving unit to receive from the subject an input that the photographic object has been recognized, and to output reception signals;
   a recognition time calculator that receives the reception signals from the receiving unit and calculates a recognition time period, which is a time period the subject requires to recognize the object;
   a challenge level data memory unit that stores challenge level data, which is data related to a predetermined challenge level of the degraded image in conjunction with recognition of the photographic object;
   a cognitive capacity calculator that conducts specified operations using the recognition time period calculated by the recognition time calculator and the challenge level data stored in the challenge level data memory unit, and calculates a cognitive capacity score, which is an index that indicates the cognitive capacity of each subject; and
   an output unit for outputting the cognitive capacity scores
   wherein the image display unit also displays the original image to the subject, and the recognition time calculator calculates a recognition time period by subtracting an original image required time period, which is the time required after the image display unit displays the corresponding original image until the receiving unit receives the input that the subject has recognized the photographic object, from the degraded image required time period, which is the time required after the image display unit displays the degraded image until the receiving unit receives the input that the subject has recognized the photographic object.

2. The cognitive capacity measurement device according to claim 1 wherein:
   the challenge level data memory unit stores as the challenge level data predetermined data that represents a normal distribution applied to a frequency distribution of a predetermined number of subjects in relation to a logarithm of the recognition time period predetermined from a statistically significant number of subjects, and
   the cognitive capacity calculator performs computations that derive and invert a sign of standardized points corresponding to the recognition time periods, which were calculated by the recognition time calculator in the time periods normal distribution specified by the challenge level data stored in the challenge level data memory unit.

3. The cognitive capacity measurement device according to claim 1 wherein a cognitive capacity memory part is further provided to relate and store the cognitive capacity score with a subject identifier to identify the subject.

4. The cognitive capacity measurement device according to claim 1 wherein the image display unit can selectively display multiple different kinds of images, and the cognitive capacity calculator calculates the cognitive capacity score from the recognition time periods obtained from each of the multiple different kinds of images.

5. The cognitive capacity measurement device according to claim 1 wherein the degraded image is one in which the original image has been degraded to represent only part of the original image.

6. The cognitive capacity measurement device according to claim 2 wherein the image display unit has a further function to display the original image to the subject, and the recognition time calculator calculates the recognition time period by subtracting the original image required time period, which is the time required after the image display unit displays the corresponding original image until the receiving unit receives the input that the subject has recognized the photographic object, from the degraded image required time period, which is the time required after the image display unit displays the degraded image until the receiving unit receives the input that the subject has recognized the photographic object.

7. The cognitive capacity measurement device according to claim 2 further comprising a cognitive capacity memory to store the cognitive capacity score with a subject identifier to identify the subject.

8. The cognitive capacity measurement device according to claim 2 wherein the image display unit selectively displays multiple different kinds of images, and the cognitive capacity calculator calculates the cognitive capacity score from the recognition time periods obtained from each of the multiple different kinds of images.

9. The cognitive capacity measurement device according to claim 2 wherein the degraded image is one in which the original image has been degraded to represent only part of the original image.

10. A degraded image challenge level measurement device comprising:
    an image display unit to display to a subject a degraded image for which specified processing has been conducted on an original image having a significant photographic object to cause the image of the photographic object to be altered;
    a receiving unit that receives from the subject an input that the photographic object has been recognized in the degraded image and outputs reception signals;
    a recognition time calculator that receives the reception signals from the receiving unit and calculates a recognition time period, which is the time required for the subject to recognize the photographic object in the degraded image;
    a recognition time data memory unit that respectively memorizes the recognition time data, which is data relating to predetermined recognition time periods of multiple subjects calculated by the recognition time calculator;
    a challenge level data calculator that calculates a challenge level data, which is data relating to the challenge level of the degraded images in conjunction with photographic object recognition, by acquiring the recognition time data stored in the recognition time data memory unit, and by using a specified function to approximate a distribution form of the recognition time; and
    a challenge level data memory unit to relate and store the challenge level data with a degraded image identifier for identifying the degraded image.

11. The degraded image challenge level measurement device according to claim 10 wherein the challenge level data calculator calculates the challenge level data using data that specifies a normal distribution that applies to a frequency distribution of the number of subjects in relation to a logarithm of the recognition time period.

12. The degraded image challenge level measurement device according to claim 10 wherein a challenge level data memory unit is further provided to relate and store the challenge level data with a degraded image identifier for identifying the degraded image.

13. A degraded image challenge level measurement device comprising:
    an image display unit to display to a subject a degraded image for which specified processing has been conducted on an original image having a significant photographic object to cause the image of the photographic object to be altered;
    a receiving unit that receives from the subject an input that the photographic object has been recognized in the degraded image and outputs reception signals;
    a recognition time calculator that receives the reception signals from the receiving unit and calculates a recognition time period, which is the time required for the subject to recognize the photographic object in the degraded image;
    a recognition time data memory unit that respectively memorizes the recognition time data, which is data relating to predetermined recognition time periods of multiple subjects calculated by the recognition time calculator; and
    a challenge level data calculator that calculates a challenge level data, which is data relating to the challenge level of the degraded images in conjunction with photographic object recognition, by acquiring the recognition time data stored in the recognition time data memory unit, and by using a specified function to approximate a distribution form of the recognition time, wherein the challenge level data calculator calculates the challenge level data using data that specifies a normal distribution that applies to a frequency distribution of the number of subjects in relation to a logarithm of the recognition time period.

14. The degraded image challenge level measurement device according to claim 13 wherein a challenge level data memory unit is further provided to relate and store the challenge level data with a degraded image identifier for identifying the degraded image.

* * * * *